United States Patent [19]
Doerr et al.

[11] Patent Number: 6,140,367
[45] Date of Patent: Oct. 31, 2000

[54] USE OF ETHYLENE DIAMINE DISUCCINATE FOR PREPARING A MEDICAMENT WITH ANTIVIRAL PROPERTIES

[75] Inventors: Hans Wilhelm Doerr, Dreieich-Buchsclag; Kai Uwe Bindseil; Lutz Müller-Kuhrt, both of Berlin; Holger Rabenau, Frankfurt; Jindrich Cinatl, Obertshausen, all of Germany

[73] Assignee: AnalytiCon AG Biotechnologie Pharmazie, Berlin, Germany

[21] Appl. No.: 09/171,836

[22] PCT Filed: Apr. 26, 1997

[86] PCT No.: PCT/EP97/02175
§ 371 Date: Jan. 19, 1999
§ 102(e) Date: Jan. 19, 1999

[87] PCT Pub. No.: WO97/40827
PCT Pub. Date: Nov. 6, 1997

[30] Foreign Application Priority Data

Apr. 27, 1996 [DE] Germany .................. 196 16 992

[51] Int. Cl.[7] .................. A01N 37/44; C07C 229/24
[52] U.S. Cl. .................. 514/566; 562/565
[58] Field of Search .................. 514/566; 562/565

[56] References Cited

FOREIGN PATENT DOCUMENTS 2 288 812A  11/1995  United Kingdom .

OTHER PUBLICATIONS

"J. Antibiotics", vol. 37, No. 4, dated Apr. 4, 1984, pp. 426–427, XP000615485, Nishikiori et al; "Production By Acinomycetes . . . ".

*Primary Examiner*—Johann Richter
*Assistant Examiner*—Brian J. Davis
*Attorney, Agent, or Firm*—Collard & Roe, P.C.

[57] ABSTRACT

Use of (S,S)-N,N'-ethylenediamine disuccinate (EDDS) of formula I

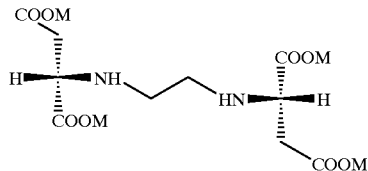

wherein M=H[+] and/or any pharmaceutically acceptable cation, for the preparation of a medicament for the treatment of cytomegaloviral infections which has immunosuppressive properties.

8 Claims, 1 Drawing Sheet

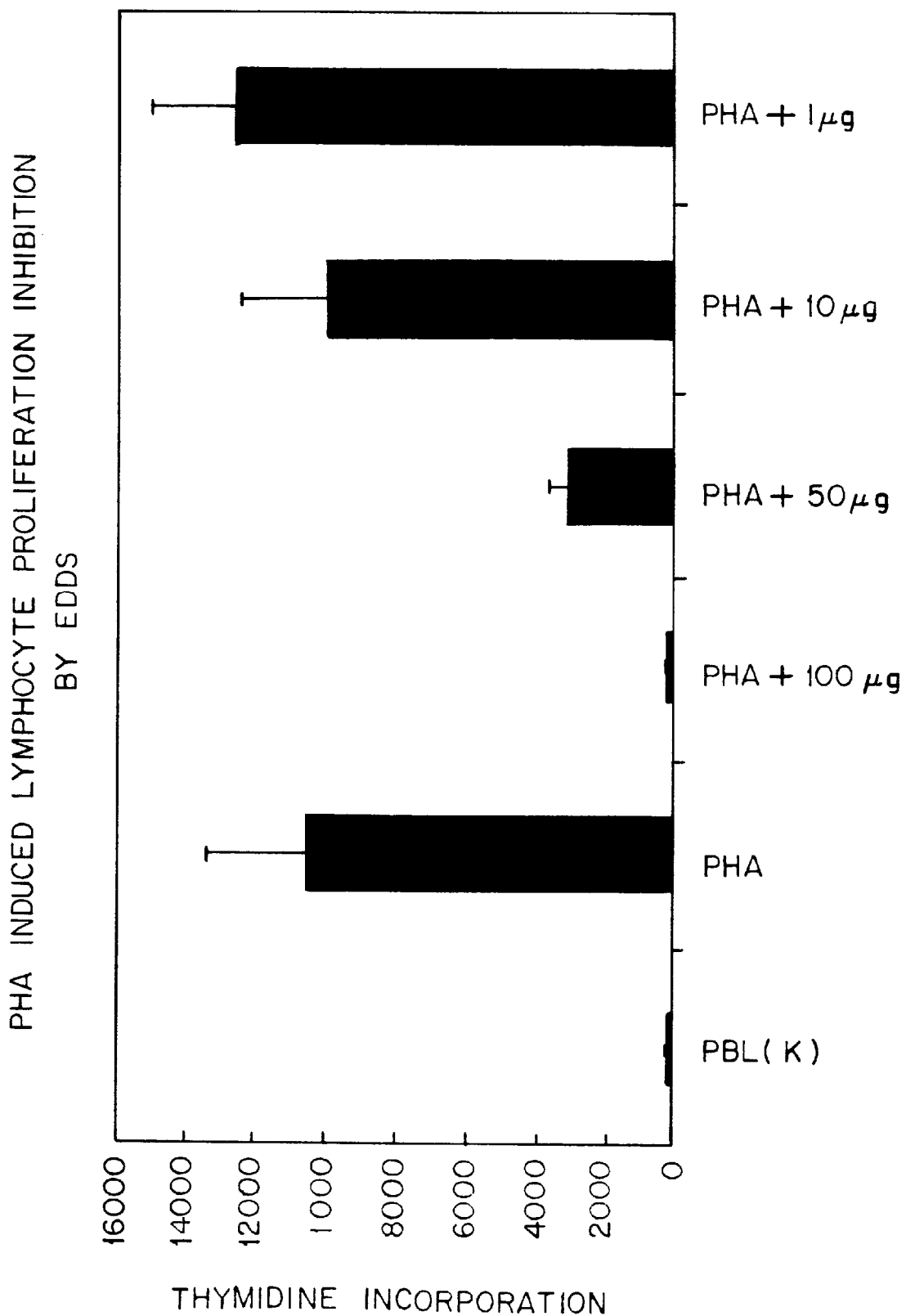

USE OF ETHYLENE DIAMINE DISUCCINATE FOR PREPARING A MEDICAMENT WITH ANTIVIRAL PROPERTIES

This application is a 371 of PCT/EP97/02175 filed Apr. 26, 1997.

BACKGROUND OF THE INVENTION

1. Field of the Invention

The present invention relates to the use of ethylenediamine disuccinate and its pharmacologically compatible salt-forming ions and its protonated form for the preparation of a medicament having antiviral properties which also has an immunosuppressive effect.

2. The Prior Art (S,S)-N,N'-ethylenediamine disuccinate is described in detail in a publication by Takaaki Nishikiori et al. (1984), The Journal of Antibiotics, Vol. 37, No. 4: 426–427. (S,S)-N,N'-ethylenediamine disuccinate can be recovered from actinomycetes and can also be prepared synthetically (J. A. Neal and N. J. Rose (1968), Inorg. Chem. Vol. 7; 2405–2412). It inhibits phospholipases C and D. If (S,S)-N,N'-ethylenediamine disuccinate is intraperitoneally administered to mice, their antibody production and DTH (delayed type hypersensitivity) reaction are suppressed. In vitro, blastogenesis of B cells and T cells is suppressed. However, this publication does not report an anti-microbial activity. The toxicity of the substance in mice is relatively low.

The cytomegaloviruses (CMV) constitute a group of related viruses which include the Herpes viruses (Lutz Schneider (1990), Pharmazeutische Zeitung, Vol. 135, No. 27, 2396–2400). After an initial infection, the viruses remain in the body in a latent condition. Only when the immune system is weakened by a immunesuppression caused by medicaments or disease, the viruses become reactivated. The name of these viruses is derived from their causing histopathologically detectable giant cells with a marginal large nucleus and containing viruses as inclusion bodies.

The viruses are ubiquitous. The percent infection of the population varies from 30% to 85% and even 95%. In adults having a functional immune system, the infection has an uneventful course and exhibits unspecifical symptoms at most, such as exhaustion and slightly increased body temperature.

In immunodeficient adults afflicted with CMV infection, pulmonary diseases, choroiditis and gastro-intestinal diseases are prevailing. In AIDS patients, CMV infections are the major cause of death.

As the incidence of CMV infections increases with increasing age, a possible participation of cytomegaloviruses in arterial plaque formation is currently being discussed. The viruses are capable of damaging endothelial cells of the vascular walls.

Various substances are discussed for treatment against cytomegaloviruses.

The publication by J. Cinatl et al. (1994), Antiviral Research, Vol. 25: 73–77, describes desferrioxamine which forms iron chelates. In in-vitro experiments, this substance can be successfully used against Herpes simplex viruses, Varicella zoster viruses, Epstein-Barr viruses and human cytomegaloviruses. The mode of action of the substance is attributed to chelate formation with iron ions. Further, cellular ribonucleotide reductase is also believed to be inhibited. However, the results obtained as yet are partly contradictory in terms of theory. The substance exhibits low toxicity.

Foscarnet is an antiviral substance having a selective activity, as detected in cell cultures, against human viruses of the Herpes group, such as Herpes simplex, Varicella zoster, Epstein-Barr and cytomegaloviruses as well as hepatitis viruses. Its antiviral activity is based on an inhibition of viral enzymes, such as DNA polymerases and reverse transcriptases. On cytomegaloviruses, foscarnet has a virostatic effect, but the viruses cannot be eliminated (Lutz Schneider (1991), Pharmazeutische Zeitung, Vol. 136, No. 46, 33–36). An essential problem of cytomegaloviral infection is the necessity of a permanent, and sometimes life-long, treatment of the patients. A further disadvantage is that cytomegaloviruses have become more resistant against this substance recently (Stanat et al. (1991), Antimicrob. Agents, Chemother., Vol. 35, No. 11: 2191–2197, and Knox et al. (1991), Lancet, Vol. 337: 1292–1293).

Ganciclovir is described in the publication by Lutz Schneider (1990), Pharmazie, Vol. 135, No. 37, 2396–2400. Ganciclovir belongs to the nucleoside antimetabolites which are derived from 2'-deoxyguanosine. Instead of 2'-deoxyribose, it bears an acyclic side chain and is distinguished from aciclovir only by an additional hydroxymethyl group in the side chain. Ganciclovir has been approved for the treatment of life-threatening or eyesight-threatening cytomegaloviral infections in patients with acquired immunodeficiency or medicamentous immunosuppression, for example, after organ transplantations. Although ganciclovir is also effective with other human-pathogenic Herpes viruses (HSV 1 and 2, Varicella zoster and Epstein-Barr), its use in such infections is out of the question because of the high side-effect level. Ganciclovir leads to neutropenia, and mice under treatment with ganciclovir have been observed to develop tumors. A further disadvantage is that that cytomegaloviruses have become more resistant against this substance recently (Stanat et al. (1991), Lancet, Vol. 337: 1292–1293).

WO 94/22438 (DINU, date of application: Dec. 29, 1993) describes diethylenetriaminepentaacetic acid for the treatment of Herpes simplex, Varicella zoster, encephalomyelitis, polyradiculoneuritis, multiple sclerosis, but not of cytomegaloviruses. Immunosuppressants, such as cyclosporin A or tacrolimus, are successfully employed in organ transplantations in order to avoid or mitigate rejection reactions. Of course, a drawback is the susceptibility of the treated patients for severe complications caused by viral and bacterial infections. In particular, in this connection, infection with cytomegaloviruses may be mentioned.

SUMMARY OF THE INVENTION

It has been the object of the present invention to provide a compound having antiviral activity which also has an immunosuppressive effect.

It was to be assumed that, in a manner similar to diethylenetriaminepentaacetic acid (Aisen and Listowsky (1980), Annu. Rev. Biochem., Vol. 49: 357–393), the substance to be used according to the invention cannot enter the cell due to its highly hydrophilic character, and therefore can complex only free metals or ions, i.e., those which are not incorporated in the cell. In contrast, desferrioxamine, for example, is known to be capable of entering the cell. Since virus replication takes place inside the cell, it had to be considered that an inhibiting drug must also enter the cell in order to become effective. Surprisingly, however, the substance according to the invention is nevertheless effective according to in-vitro experiments in a cell culture.

Particularly surprising was the result that EDDS displays an immunosuppressive activity in addition to its antiviral activity. The immunosuppressive activity is manifested in an inhibition of phytohemagglutinin stimulated lymphocyte proliferation.

BRIEF DESCRIPTION OF THE DRAWINGS

FIG. 1 shows the concentration-dependent inhibition of lymphocyte proliferation. An almost quantitative inhibition is achieved between 30 $\mu$M and 100 $\mu$M EDDS (corresponding to non-toxic concentrations).

DETAILED DESCRIPTION OF PREFERRED EMBODIMENTS

As compared to the substance diethylenetriaminepentaacetic acid, the substance to be used according to the invention is significantly more effective in terms of antiviral activity. As compared to the substance desferrioxamine, the substance according to the invention is more effective by a factor of 30.

It is further surprising that only the substance according to the invention (S,S form) can be employed as a medicament. In contrast, the other forms including modifications (propylene and glutamate) cannot be successfully employed against cytomegaloviruses.

The antiviral effect of the substance according to the invention can be modulated by the addition of ferrous and ferric ions. The antiviral activity is thereby reduced by a factor of about 2 to 3, but not completely neutralized. Thus, it is evident that the formation of iron chelates has an observable effect on the activity as an antiviral agent, but it is also evident that this effect alone cannot account for the antiviral activity.

Surprisingly, it has been found that the substance according to the invention can be employed quite selectively against cytomegaloviruses. Antivirally effective concentrations of the substance according to the invention have no influence on cellular growth. Thus, its therapeutic index is very high. Therefore, the substance according to the invention is of high clinical importance.

It is unusual that the substance according to the invention can be employed against cytomegaloviruses, but has no influence on certain other viruses, such as adenoviruses (ATTC strain: GB type 3), Varicella zoster viruses (ATCC strain: MacIntyre) and Herpes simplex viruses (HSV-Vero).

The invention further comprises the ethylenediamine succinate according to the invention and its salts and/or acidic groups. The salts inevitably result from the environment and the state of aggregation of the substance.

(S,S)-N,N'-Ethylenediamine disuccinate in which the salts comprise cations of the group having atomic numbers of 3–5, 11–13, 19–29, 37–49, or 55–81, or mixtures of the above listed cations is preferred.

More preferred is (S,S)-N,N'-ethylenediamine disuccinate in which the cations are selected from the group consisting of magnesium(II), aluminum(III), calcium(II), manganese (II), iron (II), iron(III), cobalt(II), nickel(II), copper(II), zinc(II) ions as well as lithium, potassium and sodium ions, or mixtures of the above mentioned ions. Particularly preferred are further lithium, manganese(II), calcium(II), potassium and sodium ions.

In addition, (S,S)-N,N'-ethylenediamine disuccinate in which the salts comprise organic cations is also preferred.

More preferred is (S,S)-N,N'-ethylenediamine disuccinate in which the cations are selected from the group consisting of primary, secondary or tertiary amines (e.g., ethanolamine, diethanolamine, triethanolamine, morpholine, glucamine, N,N-dimethylglucamine and N-methylglucamine), lysine, arginine or ornithine, or the cations are mixtures of the above mentioned cations.

A mixture of organic and inorganic salts is also included in the invention.

As a medicament, the substance (S,S)-N,N'-ethylenediamine disuccinate is preferred if it forms a composition with pharmacologically compatible expedients and vehicles. Such expedients and vehicles are described in Remington's Pharmaceutical Science, 15th ed., Mack Publishing Company, East Pennsylvania (1980). The compositions can be prepared by known methods.

The (S,S)-N,N'-ethylenediamine disuccinate according to the invention has pharmacological properties and can therefore be used as a pharmaceutical drug. The invention also includes a medicament containing said (S,S)-N,N'-ethylenediamine disuccinate.

In particular, the substance (S,S)-N,N'-ethylenediamine disuccinate according to the invention exhibits activity against cytomegaloviruses. The substance according to the invention shows an antiviral inhibition ($IC_{50}$ value) at concentrations of 4 $\mu$g/ml. Higher concentrations can be used without disturbing the test system. Thus, the substance according to the invention can be used in a concentration of from 0.5 to 100 $\mu$g/ml.

The experimental results of this in-vitro test show that the substance according to the invention can be used as a medicament or for medicinal treatment. These experimental results can be transferred from the in-vitro test system to an in-vivo test system without any difficulty because the antiviral test system is an established experimental design which serves for detecting antiviral activity (Gerna et al. (1992), Antiviral Res. Vol. 19: 333–345). Therefore, EDDS can be employed for the treatment or prevention of cytomegaloviral infections according to the invention, wherein the substance is also effective as an immunosuppressant. It can be used as an inhibitor in mammals, especially humans, for the treatment of the above mentioned disease.

The invention further provides (i) the use of a substance according to the invention (for preparing a medicament) as an immunosuppressant and/or for the treatment or prevention of cytomegaloviral infection;

(ii) a method for the treatment of cytomegaloviruses which comprises administering of an amount of (S,S)-N,N'-ethylenediamine disuccinate wherein said amount of ethylenediamine disuccinate is administered to a patient in need of such a medicament;

(iii) a pharmacological composition for the treatment or prevention of cytomegaloviral infection which comprises a substance according to the invention and at least one pharmaceutical expedient and/or vehicle.

The therapeutically effective dosages may vary. They depend, for example, on the salts employed, on the host, on the route of administration and on the kind and severity of the conditions to be treated.

In general, however, satisfactory results can be expected in animals if the daily doses are within a range of from 1 to 500 mg per kg of body weight. In larger mammals, for example, humans, a recommended daily dose is in the range of from 1 to 50 mg per kg of body weight; most preferably, the dose is from 5 to 30 mg per kg of body weight. For example, this dose is conveniently administered in divided doses up to four times a day. Satisfactory results are to be expected if the substance according to the invention is administered subcutaneously or intravenously. Oral administration is also possible.

EXAMPLES

The following Examples will illustrate the invention, especially the advantageous effects of the substance, but are not to be construed as limiting the invention.

Antiviral activity: cells and viruses employed

Human foreskin fibroblasts (HFF) are grown in a nutrient medium consisting of Eagle's minimal essential medium (EMEM) to which 10% fetal calf serum has been added.

The CMV laboratory strain AD169 is used. The viruses are propagated in EMEM nutrient medium to which 4% fetal calf serum has been added (maintenance medium). The virus titer is established by determining so-called immediate early antigen forming units (IEFUs) which are formed in the maintenance medium (Gerna et al. (1992), Antiviral Res. Vol. 19: 333–345).

Antiviral effect

The antiviral effect of the substances on the propagation of cytomegaloviruses is determined by different parameters:

In an ELISA (enzyme-linked immunosorbent assay), the production of CMV late antigens is determined. This result is expressed as the $IC_{50}$ value, which represents the concentration of active substance which will reduce the production rate of the antigen by 50%. The substances according to the invention have an $IC_{50}$ value of 4 µg/ml±1 µg/ml.

The cell vitality is measured in an HFF cell culture using an MTT assay. The result is expressed as the $TC_{50}$ value, which is the concentration at which 50% of the cells tested are still vital. In HFF cells, it is 435 µg/ml for the substances according to the invention.

From the two values, the quotient, $TC_{50}/IC_{50}$, is calculated to determine the therapeutic index. For the substances according to the invention, it is about 109 (Gerna et al. (1992), Antiviral Res. Vol. 19: 333–345).

Table of measured values:

| Substance | inhibitory concentration $IC_{50}$ in µg/ml | toxic concentration $TC_{50}$ in µg/ml | therapeutic index |
|---|---|---|---|
| (S,S)-N,N'-ethylene-diamine disuccinate | 4.0 | 435 | 109 |
| (R,S)-N,N'-ethylene-diamine disuccinate | 46 | ≧100* | ≧2.2 |
| (R,R)-N,N'-ethylene-diamine disuccinate | 41 | ≧100* | ≧2.2 |
| (S,S)-N,N'-propylene-diamine disuccinate | ≧100 | ≧100* | X |
| (R,R)-N,N'-propylene-diamine disuccinate | ≧100 | ≧100* | X |
| (S,S)-N,N'-ethylene-diamine diglutamate | ≧100 | ≧100* | X |
| (S,S)-N,N'-propylene-diamine diglutamate | ≧100 | ≧100* | X |
| desferrioxamine | 4.1 | 12 | 3 |
| diethylenetriamine-pentaacetic acid | 4.0 | 123 | 31 |

*highest concentration tested of the substance.
X dose which could be reached for the patient could not be determined.

The synthesis of all derivatives of N,N'-diamine disuccinate and glutamate was performed according to J. A. Neal and N. J. Rose (1968), Inorg. Chem., Vol. 7: 2405–2412.

Immunosuppressive effect

For a proliferation assay, lymphocyte cultures were started in mixed lymphocyte cultures (MLC), or with 1% phytohemagglutinin (PHA), in a total volume of 200 µl of culture medium. 18 to 20 hours before the measurement, 0.1 µCi methyl-[$^3$H]-thymidine (NEN, Germany) was added. Radiolabeled DNA was harvested on filter membranes (Schleicher & Schüll, Germany). The radioactivity was quantified with a scintillation counter (Zinsser, Germany). The sample PBL pertains to peripheral blood lymphocytes as a control.

What is claimed is:

1. A method for the treatment of infections caused by cytomegaloviruses comprising administering to a patient in need of such a treatment a therapeutically effective amount of (S,S)-N,N'-ethylenediamine disuccinate (EDDS) of formula (I)

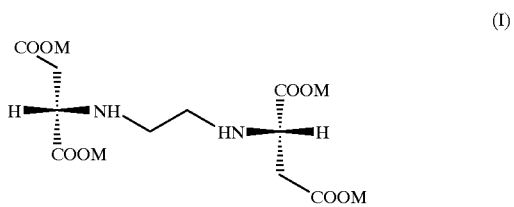

(I)

wherein M is selected from the group consisting of hydrogen, a pharmaceutically acceptable cation, and mixtures thereof.

2. The method according to claim 1, wherein said EDDS has immunosuppressive properties for the treatment of infections caused by cytomegaloviruses.

3. The method according to claim 2, wherein EDDS causes an inhibition of phytohemagglutinin stimulated lymphocyte proliferation.

4. The method according to claim 1, wherein M is selected from the group consisting of hydrogen, a cation having an atomic number of 3–5, 11–13, 19–29, 37–49, or 55–81, and mixtures thereof.

5. The method according to claim 4, wherein the cation is selected form the group consisting of magnesium(II), aluminum(III), calcium (II), manganese(II), iron(II), iron (III), cobalt(II), nickel(II), copper(II), zinc(II), lithium, potassium, sodium and mixtures thereof.

6. The method according to claim 1, wherein M comprises organic cations.

7. The method according to claim 6, wherein the cations are selected from the group consisting of primary amines, secondary amines, tertiary amines, lysine, arginine, ornithine, and mixtures thereof.

8. The method according to claim 1, wherein said EDDS is part of a composition with pharmacologically compatible expedients and vehicles.

* * * * *